United States Patent [19]

Boesten et al.

[11] Patent Number: 4,812,403

[45] Date of Patent: Mar. 14, 1989

[54] OPTICALLY ACTIVE SUBSTITUTED BUTYRAMIDE, AND PROCESS FOR THE OPTICAL SEPARATION OF SUBSTITUTED BUTYRAMIDE

[75] Inventors: Wilhelmus H. J. Boesten, Sittard; Peter J. H. Peters, Geleen, both of Netherlands

[73] Assignee: Stamicarbon B.V., Geleen, Netherlands

[21] Appl. No.: 693,352

[22] Filed: Jan. 22, 1985

[30] Foreign Application Priority Data

Feb. 2, 1984 [NL] Netherlands ............... 8400312

[51] Int. Cl.[4] .................. C12P 13/08; C12P 7/52; C07P 41/00; C12N 9/48
[52] U.S. Cl. .................................... 435/115; 435/280; 435/141; 435/212; 435/863; 435/228
[58] Field of Search ............ 435/280, 863, 115, 141, 435/227, 228, 170, 212, 106

[56] References Cited

U.S. PATENT DOCUMENTS

| | | | |
|---|---|---|---|
| 3,971,700 | 7/1976 | Boesten | 435/280 |
| 4,080,259 | 3/1978 | Boesten et al. | 435/106 |
| 4,443,548 | 4/1984 | Oshima et al. | 435/280 |
| 4,481,362 | 11/1984 | Nakai et al. | 548/498 |
| 4,497,957 | 2/1985 | Nakai et al. | 548/496 |

FOREIGN PATENT DOCUMENTS

| | | | |
|---|---|---|---|
| 0043211 | of 1982 | European Pat. Off. | 435/108 |
| 2700270 | of 1978 | Fed. Rep. of Germany | 435/108 |

OTHER PUBLICATIONS

PCT Publication WO 80/01571, published Aug. 7, 1980, (w/English abstract).

*Primary Examiner*—Charles F. Warren
*Assistant Examiner*—Irene Marx
*Attorney, Agent, or Firm*—Cushman, Darby & Cushman

[57] ABSTRACT

Process for preparing D-2-amino-2,3-dimethylbutyramide and/or L-2-amino-2,3-dimethylbutyric acid, wherein an aqueous solution of DL-2-amino-2,3-dimethylbutyramide is contacted with a preparation containing an aminoacyl amidase which has been obtained from a culture of *Mycobacterium neoaurum* and in that subsequently D-2-amino-2,3-dimethylbutyramide and/or L-2-amino-2,3-dimethyl-butyric acid is (are) recovered from the resulting hydrolysis mixture. The compound D-2-amino-2,3-dimethylbutyramide is novel.

4 Claims, No Drawings

OPTICALLY ACTIVE SUBSTITUTED BUTYRAMIDE, AND PROCESS FOR THE OPTICAL SEPARATION OF SUBSTITUTED BUTYRAMIDE

FIELD OF THE INVENTION

The invention relates to the compound D-2-amino-2,3-dimethylbutyramide. As an optically active compound this is a novel compound. This compound D-2-amino-2,3-dimethylbutyramide in this respect is deemed to include all mixtures, liquid and solid, and solutions and in general every composition wherein 2-amino-2,3-dimethylbutyramide is present in the D-form for more than 50%. The invention also relates to a process for the preparation of D-2-amino-2,3-dimethylbutyramide and-/or L-2-amino-2,3-dimethylbutyric acid. These compounds can also be called D-α-methylvaline amide and L-α-methylvaline, respectively.

BACKGROUND OF THE INVENTION

It is known that certain enzymes are capable of hydrolyzing α-amino acids amides in an aqueous medium to α-amino acids. These so-called α-aminoacyl amidases (α-aminoacyl peptide hydrolase EC 3.4.11), also called aminopeptidases, show, like most enzymes, a very strong stereospecific activity and effect the hydrolysis of L-α-amino acid amides only. D-α-amino acid amides are either not hydrolyzed at all, or are hydrolyzed extremely slowly.

Aminoacyl amidases can be used for instance for the optical separation of amino acids, by contacting a DL-α-amino acid amide with the aminoacyl amidase and isolating the hydrolysis product L-α-amino acid and/or the D-α-amino acid amide; see Greenstein and Winitz, 'Chemistry of the amino acids', vol. 3, pp. 1778–1781 (New York 1961).

From U.S. Pat. No. 3,971,770 it is known that DL-amino acid amides can be separated into the corresponding D-amino acid amides and L-amino acids in the presence of an aminopeptidase preparation obtained from a culture of *Pseudomonas putida*.

However, in general the optical separation of α-amino acid amides containing an α-methyl group is not such a simple process. For instance, Tetrahedron Letters Vol. 23, No. 33, pp. 3335–3336 (1982) gives a description showing that the introduction of an α-methyl group into a good substrate for chymotrypsin, e.g. acetyl-L-tyrosine amide, makes the enzymatic hydrolysis rate of this substrate decrease by a factor of $10^5$. This decrease is believed to have to do with an unfavourable orientation of the bond to be split with respect to the active centre (steric hindrance due to the methyl group). Further, the applicant has found that separation of DL-2-amino-2,3-dimethylbutyramide does not take place in the presence of a preparation obtained from *Pseudomonas putida* and containing an aminoacyl amidase.

SUMMARY AND OBJECT OF THE INVENTION

The object of the invention is finding an enzyme-containing preparation capable of selectively separating DL-2-amino-2,3-dimethylbutyramide into D-2-amino-2,3-dimethylbutyramide and L-2-amino-2,3-dimethylbutyric acid. The invention is based on the use of such a preparation.

The present invention provides a process for preparing D-2-amino-2-3-dimethylbutyramide and/or L-2-amino-2,3-dimethylbutyric acid by contacting an aqueous solution of DL-2-amino-2,3-dimethyl-butyramide with a preparation containing aminoacyl amidase to obtain a hydrolysis mixture and thereafter recovering D-2-amino-2,3-dimethylbutyramide and/or L-2-amino-2,3-dimethylbutyric acid from the hydrolysis mixture. The aminoacyl amidase is obtainable from a culture of *Mycobacterium neoaurum*.

DESCRIPTION OF THE INVENTION

The process according to the invention the present invention provides a process for preparing D-2-amino-2,3-dimethylbutyramide and of L-2-amino-2,3-dimethylbutyric acid which is characterized in that an aqueous solution of DL-2-amino-2,3-dimethylbutyramide is contacted with a preparation containing an aminoacryl amidase which has been obtained from a culture of *Mycobacterium neoaurum* and in that subsequently D-2-amino-2,3-dimethylbutyramide and/or L-2-amino-2,3-dimethylbutyric acid is (are) recovered from the resulting hydrolysis mixture.

In the enzymatic hydrolysis of DL-2-amino-2,3-dimethylbutyramide according to the invention, hydrolysis affects practically exclusively the L-form, so that the hydrolysis mixture contains mainly the D-amide and the L-acid. Processing of the hydrolysis mixture to the D-amide and/or the L-acid can be done in a way known per se, for instance by the use of a selective solvent or by crystallization. The processing of the D-amide and/or the L-acid may be carried to the point where these compounds are available in the form of crystals. It is possible to process these compounds to obtain a solution or suspension.

D-2-amino-2,3-dimethylbutyramide can be used as a functional group inthe preparation of herbicides of the type 2-(5-butyl-2-pyridyl)-5-isopropyl-5-methyl-2-imidazolin-4-one, as described for instance in Example 17 of EP-A 41623.

L-2-amino-2,3-dimethylbutyric acid does not racemize in normal reactions. Consequently, the N-acyl derivative of this L-acid, for instance, can quite well be produced and then used as an optically active auxiliary in diastereoisomeric salt formation.

Enzyme preparations showing α-aminoacylamidase activity can be obtained from animal organs, for instance neat's eyes or pig kidneys, or by a microbiological process. The α-aminoacylamidase can, according to the invention, in general be used in its pure form or as a crude preparation. If so desired, the enzyme can be immobilized by absorption on or chemical bonding to a carrier.

Particularly suitable for making preparations showing α-aminoacylamidase activity according to the invention is *Mycobacterium neoaurum* ATCC 25795.

*Mycobacterium neoaurum* can be cultivated in the media usually employed. It is advantageous to add to such a medium a normally used yeast extract, so as to raise the yield of the culture, and also L- or DL-2-amino-2,3-dimethylbutyramide.

In all probability, the enzyme having aminoacylamidase activity is produced intracellularly. An indication for this is the fact that the medium in which *Mycobacterium neoaurum* was cultivated showed hardly any α-aminoacylamidase activity. In the application of this enzyme use may be made of whole cells, freeze-dried or not. It is also possible to make the cell wall permeable in a known way, which makes for a more efficient hydrolysis process. It is, further, possible to use an extract free of cells. If so desired, the enzyme can be recovered in pure form from the cell-free extract in a way known per se. With the abovementioned applications of the enzyme, use may be made of known immobilization techniques, as described for instance in 'Applied Biochemistry and Bioengineering', Vol. 1 (1976) and Vol. 4 (1983), Academic Press.

The hydrolysis may be carried out at a temperature of between 0° C. and 60° C., by preference between 20° C. and 45° C., and at a pH of between 8 and 11.5, because under these conditions hydrolysis is fastest.

The duration of the hydrolysis may vary from, e.g., 10 to 100 hours. If the hydrolysis duration is long, however, it is possible for some D-amide still to be hydrolyzed to the corresponding D-acid.

The invention will be further explained by means of the following examples.

EXAMPLES

Preparation of a culture of *Mycobacterium neoaurum* ATCC 25795

In a 10-liter fermenter there were introduced, per 1000 ml water, 10 g glucose, 2 g yeast extract (commercially available as Difco 0127-01), 2 g casitone (Difco 0259-02), 1 g beef extract (Difco 0126-01), 1.5 g DL-2-amino-2,3-dimethylbutyramide, 1 g of a surfactant commercially obtainable under the name of Tween 80, and 5 g $K_2HPO_4$, and the whole was brought to pH 7.2. After sterilization for 40 minutes at 110° C. and after cooling to 30°–40° C., the fermenter was seeded with 500 ml of a pre-culture of *Mycobacterium neoaurum* ATCC 25795 (same medium), and stirring was applied for 80 hours at 30°–40° C. The pH was meanwhile kept constant at 7.2, with 1N NaOH or 1N $H_2SO_4$, in dependence on the direction of the change in pH.

After this culture period the resulting cells were centrifuged and twice washed with distilled water. Thereafter the cells were frozen at −80° C. and freeze-dried, within 1 hour. The yield of freeze-dried cells was 3 grams per liter.

EXAMPLE I

An amount of 30.0 g of *Mycobacterium neoaurum* ATCC 25795 as obtained according to the above description was added, in the form of freeze-dried cells, to a solution of 200.0 g DL-2-amino-2,3-dimethylbutyramide (1.54 mol) in 1800 ml distilled water (pH=10.7). Next, stirring was applied for 72 hours at 37° C. The hydrolysis mixture obtained in this way was centrifuged to remove the cell material. The resulting clear supernatant aqueous layer was decanted and subjected to evaporation at 50° C. and 16 mbar. The resulting evaporation residue (192.1 g) was stirred for 90 minutes with 600 ml dichloromethane. The result was that D-2-amino-2,3-dimethylbutyramide did dissolve inn dichloromethane, whilst L-2-amino-2,3-dimethylbutyric acid did not. The resulting suspension was filtered on a glass filter and washed on the filter with 4×100 ml dichloromethane. The filtrate was then subjected to evaporation at 40° C. and 16 mbar. The yield of D-2-amino-2,3-dimethylbutyramide was 92.3 g (0.71 mol). The yield of pure D-2-amino-2,3-dimethylbutyramide—purity determined by means of thin-layer chromatography (TLC)—was 92.3%. The specific rotation of the D-2-amino-2,3-dimethylbutyramide was:

$[\alpha]_D^{20} = +26.5°$ C. (C=2.0; water).

In order to determine the optical purity and the configuration, 6.5 g D-2-amino-2,3-dimethylbutyramide (0.05 mol) was hydrolyzed in 2600 ml 6N hydrochloric acid at 90° C. for 64 hours. The acid hydrolysis product was then subjected to evaporation at 50° C. and 16 mbar, after which the residue was dissolved in 200 ml water. The solution thus obtained was passed across a strongly basic ion exchanger having a volume of 200 ml (commercially obtainable as Dowex 1). The ion exchanger was washed with 650 ml distilled water, and the D-2-amino-2,3-dimethylbutyric acid formed by hydrolysis was eluted with 250 ml 6N acetic acid. The ion exchanger was subjected to an after-washing treatment with 400 ml distilled water. Evaporation of the acetic eluate at 40° C. and 16 mbar yielded 6.6 g of evaporation residue. This residue was stirred with 100 ml acetone and next filtered on a glass filter. On this filter the residue was subsequently washed with 4×25 ml acetone. After drying at 50° C. and 16 mbar, 6.4 g D-2-amino-2,3-dimethylbutyric acid was found (yield 97.7%).

The specific rotation of this D-2-amino-2,3-dimethylbutyric acid, which was pure as tested by TLC, was:

$[\alpha]_D^{25} = +4.0°$ (C=1.31; water).

J. Org. Chem., Vol. 40. No. 7, p. 954 (1975) mentions a specific rotation of $[\alpha]_D^{25} = +3.9°$ (C=1.31; water).

This means that the optical purity of the D-2-amino-2,3-dimethylbutyric acid is higher than so far mentioned in literature.

COMPARATIVE EXAMPLE I

Example I was repeated with 30.0 g of freeze-dried *Pseudomonas putida* ATCC 12633 as enzyme source. The pH was adjusted to 9.0, after which stirring was applied at 40° C. for 72 hours. By means of TLC and HPLC (high pressure liquid chromatography) no L-2-amino-2,3-dimethylbutyric acid was demonstrable.

EXAMPLE II

A solution of 20.8 g DL-2-amino-2,3-dimethylbutyramide (0.16 mol) in 350 ml distilled water (pH=10.7) was brought to pH 8.5 by means of 1.8 ml sulphuric acid (96% by weight). To this solution 2.0 g *Mycobacterium neoaurum* ATCC 25795 was added in the form of freeze-dried cells, after which stirring was applied for 65 hours at 40° C. Next, the resulting hydrolysis mixture was filtered on a glass filter in order to remove the cell remnants. The filtrate was passed across a strongly basic ion exchanger having a volume of 200 ml (commercially obtainable as Dowex 1), and an elution with 200 ml distilled water was carried out. Evaporation of the eluate at 50° C. and 16 mbar yielded 10.2 g (0.078 mol) D-2-amino-2,3-dimethylbutyramide. TLC analysis showed this product to be pure. The yield was 98.1%.

The specific rotation of the resulting D-2-amino-2,3-dimethylbutyramide was:

$[\alpha]_D^{20} = +26.4°$ (C=2.0; water).

Given the maximum $[\alpha]_D^{20}$ value of Example I, it is easy to calculate the selectivity:

Selectivity as % D-amide:

$$50\% + \frac{[\alpha]_D^{20} \cdot 50\%}{[\alpha]_D^{20} \text{ max}} = 50\% + \frac{26.4 \cdot 50\%}{26.5} = 99.8\%.$$

The L-2-amino-2,3-dimethylbutyric acid formed by the hyrolysis was removed from the strongly basic ion exchanger by elution with 250 ml of 4N acetic acid. After washing of the ion exchanger with 250 ml distilled water the acid eluate was subjected to evaporation at 40° C. and 16 mbar. The evporation residue (10.4) g was stirred with 100 ml acetone and filtered on a glass filter. The yield of L-2-amino-2,3-dimethylbutyric acid was 10.3 g (TLC-pure, yield 99.0%).

The specific rotation of the L-2-amino-2,3-dimethylbutyric acid formed was:

$[\alpha]_D^{20} = -3.4°$ (C=1.31; water).

Selectivity as L-acid: 93.6%. This was calculated in the way described above for the D-amide. The $[\alpha]_{D-max}^{20}$ for the D-acid was based on the value of $-3.9°$ for the L-acid from from literature.

That the measurement showed the L-2-amino-2,3-dimethylbutyric acid not to possess perfect optical purity is presumably due to the long duration of the reaction in this example. This causes some D-amide to be enzymatically hydrolyzed to the D-acid after all. In the processing phase this D-acid gets into the fraction which also contains the L-acid.

We claim:

1. The process for preparing D-2-amino-2,3-dimethylbutyramide and/or L-2-amino-2,3-dimethylbutyric acid comprising:

enzymatically hydrolyzing DL-2-amino-2,3-dimethylbutyramide by contacting an aqueous solution of DL-2-amino-2,3-dimethylbutyramide with a preparation containing an aminoacyl amidase obtained from a culture of *Mycobacterium neoaurum* ATCC 25795 whereby a hydrolysis mixture is obtained; and recovering D-2-amino-2,3-dimethylbutyramide and/or L-2-amino-2,3-dimethylbutyric acid from the thus obtained hydrolysis mixture.

2. Process according to claim 1, characterized in that the hydrolysis is carried out at a pH of 8–11.5 and at a temperature of 20°–45° C.

3. Process according to claim 1, characterized in that *Mycobacterium neoaurum* is used in the form of freeze-dried cells.

4. The process according to claim 2, wherein said culture of *Mycobacterium neoaurum* is used in the form of freeze-dried cells.

* * * * *